United States Patent [19]

Costantini et al.

[11] Patent Number: 5,756,837

[45] Date of Patent: May 26, 1998

[54] METHOD OF RECYCLING A CATALYST IN A REACTION INVOLVING THE DIRECT OXIDATION OF CYCLOHEXANE INTO ADIPIC ACID

[75] Inventors: Michel Costantini, Lyons; Eric Fache, Villeurbanne; Daniel Nivert, Seyssuel, all of France

[73] Assignee: Rhone-Poulenc Fiber & Resin Intermediates, Courbevoie Cedex, France

[21] Appl. No.: 765,826

[22] PCT Filed: Jul. 13, 1995

[86] PCT No.: PCT/FR95/00944

§ 371 Date: Feb. 26, 1997

§ 102(e) Date: Feb. 26, 1997

[87] PCT Pub. No.: WO96/03365

PCT Pub. Date: Feb. 8, 1996

[30] Foreign Application Priority Data

Jul. 21, 1994 [FR] France ................................ 94 09253

[51] Int. Cl.⁶ .......................... C07C 51/31; C07C 51/00; C07C 51/42

[52] U.S. Cl. ..................... 562/543; 562/590; 562/593

[58] Field of Search ........................... 562/543, 590, 562/593

[56] References Cited

U.S. PATENT DOCUMENTS

| 2,223,493 | 12/1940 | Loder | 562/543 |
| 4,202,797 | 5/1980 | Jones | 252/413 |

FOREIGN PATENT DOCUMENTS

| 2 386 346 | 11/1978 | France . |
| 94/07833 | 4/1994 | WIPO . |
| 94/07834 | 4/1994 | WIPO . |

*Primary Examiner*—Gary Geist
*Assistant Examiner*—Rosalynd Keys
*Attorney, Agent, or Firm*—Burns, Doane, Swecker & Mathis, L.L.P.

[57] ABSTRACT

A process for recycling a catalyst containing cobalt including treating a reaction mixture obtained during the direct oxidation of cyclohexane to adipic acid by extracting at least some of the glutaric acid and succinic acid which are formed in the reaction.

30 Claims, No Drawings

METHOD OF RECYCLING A CATALYST IN A REACTION INVOLVING THE DIRECT OXIDATION OF CYCLOHEXANE INTO ADIPIC ACID

This application was filed as a 35 U.S.C. §371 of PCT/FR95/00944, which designated the United States.

The present invention relates to the field of the one-step oxidation of cyclohexane to adipic acid, using a gas containing oxygen, in liquid phase and in he presence of a catalyst containing cobalt.

The direct oxidation of cyclohexane to adipic acid is a process which has been worked at for a long time, in particular on account of the obvious advantages there would be in converting cyclohexane into adipic acid, in a single step and without using an oxidant such as nitric acid, this compound generating nitrogen oxides which must then be treated in order to avoid any contamination.

Thus, American patent U.S. Pat. No. 2,223,493, published in December 1940, describes the oxidation of cyclic hydrocarbons to corresponding diacids, in a liquid phase generally containing acetic acid, at a temperature of at least 60° C., using a gas containing oxygen and in the presence of an oxidation catalyst such as a cobalt compound. This patent makes provision for a separation of the adipic acid formed by crystallization, but teaches nothing about the manner of recycling the catalyst, in a new oxidation operation, and less still about the activity which a catalyst that has been recycled one or more times would have.

Patent Application WO-A-94/07833 describes a similar process, specifying that the solvent represents less than 1.5 mol per mole of cyclic hydrocarbon, that the said solvent comprises an organic acid having only primary or secondary hydrogen atoms and that the reaction is carried out in the presence of at least 0.002 mol of cobalt-based catalyst per 1000 g of reaction mixture. At the end of the reaction, the diacid formed in isolated.

Patent Application WO-A-94/07834, filed on the same day as the above patent application, also describes the same process, but develops the phases for the treatment of the final reaction mixture. This treatment consists in separating the diacid formed, by cooling the mixture in order to bring about precipitation of the said diacid, and in separating by filtration the diacid from two liquid phases, a non-polar one which is recycled, and a polar one which is also recycled after an optional hydrolysis and a separation of an additional mount of diacid.

These various patents present solutions which allow the one-step oxidation of cyclohexane to adipic acid with an industrially acceptable selectivity, but they do not address the specific problem of the progressive and relatively rapid deactivation of the catalyst during its recycling.

Indeed, when the reaction mixture obtained from the cyclohexane oxidation reaction is cooled in order to crystallize some of the adipic acid, and then filtered in order to separate out this precipitated adipic acid, the filtrate thus obtained contains the catalyst, residual adipic acid, the reaction by-products (especially glutaric acid, succinic acid, cyclohexanol, cyclobextaone, hydroxycaproic acid and cyclohexyl esters), the arencted cyclohexane, the acetic acid solvent and the water formed.

Some of these various compounds definitely influence the deactivation of the catalyst. In the process described in Patent Application WO-A-94/07834, the larger part of these various compounds is recycled to the oxidation, optionally after addition of further amounts of cyclohexane and optionally after separation of an additional amount of adipic acid remaining in the mixture. It turns out that when the catalyst and the various by-products are recycled in a new oxidation reaction, relatively rapid deactivation of the catalyst is observed. Thus, it is indicated in the various examples of WO-A-94/07834 that the rate of formation of the adipic acid decreases by 26% to 43% after four cycles of the catalyst.

One of the subjects of the present invention is thus to allow the recycling of the cobalt catalyst with little or no deactivation.

In order to achieve this aim, the process of the invention includes a step for the treatment of the reaction mixture obtained during the direct oxidation of the cyclohexaue to adipic acid, consisting of an extraction of at least some of the glutaric acid and succinic acid which are formed in the reaction.

A first subject of the invention consists first of all of a process for recycling a catalyst containing cobalt, in a reaction for the direct oxidation of cyclohexane to adipic acid, in a solvent comprising at least one aliphatic carboxylic acid having only primary or secondary hydrogen atoms, by a gas containing oxygen, the said recycling process being characterized:

- in that the reaction mixture derived from a prior operation for the oxidation of the cyclohexane to adipic acid in treated in order to remove the more volatile compounds, optionally after the crystallization and separation of at least some of the adipic acid which it contains,
- in that the residue obtained is extracted using a solvent, chosen from ketones, alcohols, esters, various mixtures thereof or mixtures of hydrocarbon and carboxylic acid, this solvent being capable of dissolving all or a large part of the diacids contained in the said residue,
- in that the extraction residue thus obtained, containing the larger part of the cobalt catalyst, is used in a new operation for the oxidation of cyclohexane to adipic acid, after addition of the necessary complements of cyclohexane, of carboxylic acid and, where appropriate, of cobalt catalyst.

In the present text, the term "large part" means at least 50% by weight of the total amount of the compound or compounds under consideration.

The reaction mixture may conveniently be treated by distillation, at atmospheric pressure or at reduced pressure, of the more volatile compounds which are especially the unreacted cyclohexane, the carboxylic acid serving as solvent in the oxidation reaction, the water formed and certain intermediate compounds such as cyclohexanol and cyclohexanone. An mentioned previously, this treatment may be preceded by the crystallization of some or all of the adipic acid, via cooling of the reaction mixture, and by its separation, for example via filtration or centrifugation.

The ketones which may be used to extract the catalyst from the residue obtained are especially acetone, methyl ethyl ketone and cyclohexanone, cyclohexanone being preferred since it can, if required, be reused in other stages of the process, for example it can be recycled in the oxidation.

The alcohols which may be used to extract the catalyst from the residue obtained are especially 1-propanol, 2-propanol, 1-butanol, 2-butanol, tert-butanol and cyclohexanol, cyclohexanol being preferred since it can, if required, be reused in other stages of the process, for example it can be recycled in the oxidation.

The esters which may be used to extract the catalyst from the residue obtained are especially esters derived from the alcohols mentioned above with aliphatic carboxylic acids having only primary or secondary hydrogen atoms, such as those which are used in the cyclohexane oxidation reaction.

Mixtures of several of these extraction solvents may, of course, be used, especially mixtures of cyclohexanol and cyclohexanone (sometimes referred to as olone). Other solvent mixtures may also be suitable, for example mixtures of aliphatic or cycloaliphatic hydrocarbons and of carboxylic acids, which will be defined below.

A second subject of the invention also consists of a process for recycling a catalyst containing cobalt, in a reaction for the direct oxidation of cyclohexane to adipic acid, by a gas containing oxygen, the said recycling process being characterized:

in that the reaction mixture, obtained from a prior operation of oxidation of the cyclohexane to adipic acid, from which mixture at least some of the intermediate oxidation products, especially such as cyclohexanol and cyclohexanone, some carboxylic acid solvent and water has been separated and from which mixture at least some of the adipic acid formed has been recovered by crystallization, is subjected to at least one extraction using at least one cosolvent or using a mixture comprising a coaolvent and a carboxylic acid, in that there are separated, on the one hand, a mixture containing at least some of the cobalt catalyst, some of the carboxylic acid and possibly residual amounts of other compounds and, on the other hand, a solution containing the cosolvent and at least some of the glutaric acid and succinic acid which are formed in the oxidation reaction, as well as some carboxylic acid, and in that the mixture containing at least some of the cobalt catalyst is used in a new operation for the oxidation of cyclohexane to adipic acid, optionally after the addition of extra cobalt catalyst.

The cosolvents which may be used in the process according to the second subject of the invention are generally chosen from hydrocarbons, especially aliphatic and cycloaliphatic hydrocarbons, ketones and alcohols.

Among the hydrocarbons, there may be mentioned hexane, heptane, octane, nonane, decane, undecane, dodecane and cyclohexane.

Among the ketones, those which have been mentioned for the extraction of the residue in the process according to the first subject of the invention may be used, cyclohexanone being preferred.

Among the alcohols, those which have been mentioned for the extraction of the residue in the process according to the first subject of the invention may be used, cyclobexanol being preferred.

It is preferable to use cyclohexane as cosolvent in the process according to the second subject of the invention, since this facilitates the treatment of the various solutions obtained during the process and their possible recycling in the oxidation reaction.

The crude reaction mixture which, after certain separation operations, is used in the process of the invention, is obtained from the oxidation known per se of cyclohexane, by a gas containing oxygen, in a liquid medium comprising a carboxylic acid and in the presence of a catalyst containing cobalt.

For the preparation of this crude reaction mixture, reference may be made to the processes described in the prior art, especially in the abovementioned U.S. Pat. No. 2,223,493. Thus, the initial cyclohexane/carboxylic acid weight ratio may, for example, be between 0.1/1 and 10/1 and preferably between 0.5/1 and 3/1. The cobalt catalyst preferably comprises a cobalt compound which is soluble in the reaction medium, chosen for example from cobalt carboxylates, preferably such as cobalt acetate tetrahydrate, cobalt chloride, cobalt bromide and cobalt nitrate.

The amount of catalyst, expressed as a weight percentage of cobalt relative to the reaction mixture, is generally between 0.01% and 5% and preferably between 0.05% and 2%, without these values being critical. It is, however, a question of having a sufficient activity while not using excessive amounts of a catalyst which must then be separated from the final reaction mixture and recycled.

Besides cobalt, the catalyst may also contain other compounds based on metals such an manganese and/or copper and/or cerium and/or vanadium.

It is advantageous also to use an initiator compound for the oxidation reaction, for example such as a ketone or an aldehyde. Cyclohexanone, which is a reaction intermediate, is most particularly mentioned. The initiator generally represents from 0.01% to 20% by weight of the weight of the reaction mixture used, without these proportions having a critical value. The initiator is especially useful when starting the oxidation and when the cyclohexane is oxidized at a temperature below 120° C. It may be introduced at the start of the reaction.

The carboxylic acid acting an solvent in the cyclohexane oxidation reaction is more particularly a saturated aliphatic carboxylic acid having from 2 to 9 carbon atoms and having only primary or secondary hydrogen atoms.

Acetic acid is preferably used as solvent for the cyclohexane oxidation reaction. In the rest of the present description, acetic acid will be referred to for convenience as the carboxylic acid used in the various steps of the process.

The oxidation may also be carried out in the presence of water introduced in the initial stage of the process.

The cyclobexane oxidation reaction is generally carried out at a temperature of from 60° C. to 180° C. and preferably of from 70° C. to 120° C.

The pressure is not a critical parameter of the reaction and is generally between 10 kPa (0.1 bar) and 10,000 kPa (100 bar).

Before performing the extraction operation according to the invention, the crude reaction mixture obtained from oxidation of the cyclohexane in subjected to various operations for the separation of some of its constituents.

According to a first variant of the process according to the second subject of the invention, the crude reaction mixture may first be subjected to cooling to a temperature of 16° C. to 30° C. for example, which brings about the crystallization of at least some of the adipic acid formed. A three-phase medium is thus obtained comprising a solid phase essentially consisting of adipic acid, an upper cyclohexane liquid phase essentially containing the unreacted cyclohexane and a lower acetic liquid phase essentially containing the acetic acid, the water formed, adipic acid, the cyclohexane oxidation intermediates such as cyclohexanol, cyclohexanone and hydroxycaproic acid, by-products such as glutaric acid and succinic acid, and the cobalt catalyst. The medium obtained by cooling the reaction mixture may, where appropriate, be a two-phase medium, that is to say that it contains only the precipitated adipic acid and the acetic phase, if the conversion of the cyclohexane during the oxidation is complete or almost complete.

After filtration or centrifugation of the solid, the two liquid phases constituting the filtrate or the centrifugate are separated by settling, if need be: the cyclohexane phase, which contains small amounts of cyclohexane oxidation products, may be recycled in a new oxidation reaction.

It may also be advantageous to concentrate the reaction mixture, prior to the adipic acid crystallization operation; a single acetic liquid phase may then be found, during the precipitation of the adipic acid.

According to a second variant of the process according to the second subject of the invention, the final crude reaction mixture may be removed while hot, for example at a temperature which may be up to 75° C. The reaction mixture then separates into two liquid phases by settling: an upper cyclohexane phase essentially containing the unreacted cyclohexane and a lower acetic liquid phase essentially containing the acetic acid, the adipic acid, the water formed, the cyclohexane oxidation intermediates such as cyclohexanol, cyclohexanone and hydroxycaproic acid, by-products such as glutaric acid and succinic acid, and the cobalt catalyst.

As in the first variant, the two liquid phases are separated by settling: the cyclohexane phase, which contains small amounts of cyclohexane oxidation products, may be recycled in a new oxidation reaction.

The comment made above for the first variant is also valid for the other variants: if the cyclohexane used in the oxidation is virtually all converted, there cannot be two liquid phases there, but only a single acetic phase.

After possible eoncentration, the acetic phase is then cooled to a temperature of 16° C. to 30° C. for example, which causes the crystallization of at least some of the adipic acid formed, which is then separated by filtration or centrifugation. This adipic acid may be purified by recrystallization from a suitable solvent, which may advantageously be acetic acid or water. When acetic acid is used as the recrystallization solvent, it may then be added to the acetic phase obtained above.

According to a third variant of the process according to the second subject of the invention, a water/cyclohexane azeotropic mixture may be distilled off during the oxidation reaction and, after separation of this mixture by settling, the cyclohexane may then, if so desired, be reintroduced into the reactor. This allows at least some of the water to be removed from the reaction mixture. The final crude reaction mixture may then be treated according to the first variant described above, that is to say by cooling in order to precipitate the adipic acid, filtration or centrifugation. The consequence of removing the water is to avoid the possible separation of the liquid part into two distinct phases on settling. The single liquid phase obtained is then treated in the same way as the acetic phase.

The acetic phase, obtained in one or other of these three variants for the treatment of the final crude reaction mixture, is subjected to an extraction with cycloboxane, either such as it is obtained after separation by settling (especially in the case where the water has been removed therefrom), or preferably after having been concentrated by heating to a temperature of 30° C. to 80° C. at reduced pressure. This concentrating makes it possible to remove some of the acetic acid, at least the majority of the water and at least some of the light compounds which may be present, such an some of the cyclohexane, of the cyclohexanol or of the cyclohexanone. The compounds thus separated from the acetic phase may be recycled in the cyclohexane oxidation step, either in total or after separation of at least some of the water which they contain. Generally, concentrating reduces the acetic phase to a volume representing from 80% to 10% of its initial volume, these values being given merely as examples. One variant consists in concentrating to dryness the acetic phase, that is to say in removing all of the acetic acid which it contains.

Partial concentration of the acetic phase may also allow, if it is followed by a cooling under the conditions indicated above for the crystallization of the adipic acid, an additional amount of adipic acid to be precipitated.

The concentrated or non-concentrated acetic phase is extracted either with cyclohexane alone or with cyclohexane/acetic acid mixtures. The essential point is, however, that the mixture consisting of the acetic phase subjected to the extraction and of the cyclohexane should have an overall cyclohexane/acetic acid weight ratio between 1/1 and 50/1 and preferably between 2/1 and 15/1. This means that, depending on the composition of the acetic phase obtained after the various treatments of the reaction mixture which are described above, the acetic acid required to extract the composition thus defined with a cyclohexane/acetic acid mixture will consist partly or totally of the acetic acid contained in the acetic phase or will be introduced with the cyclohexane in the case where the acetic acid of the said acetic phase has been removed.

The extraction may be performed one or more times or, within the context of a continuous process, by the usual industrial techniques. It may be carried out at a temperature ranging up to the boiling point of the solvent or solvents used. The extraction is generally performed between 10° C. and 80° C. and preferably between 50° C. and 80° C.

The extraction operation gives, on the one hand, a solution which contains at least some of the glutaric acid and succinic acid which it is desired to separate out, as well as residual amounts of other by-products which may still remain, such as lactones, esters and products of over-oxidation, and, on the other hand, a mixture essentially containing the cobalt catalyst. This mixture is generally separated by settling.

The cobalt catalyst thus separated out is recycled in a new cyclohexane oxidation reaction, optionally after a further addition to compensate for the losses suffered during the various treatments of the reaction mixture obtained from the cyclohexane oxidation.

This catalyst remains as active as the new catalyst used in the first cyclohexane oxidation operation and it may thus be recycled a large number of times without considerably decreasing its activity and the selectivity of the reaction to form acetic acid.

A third subject of the invention consists of a continuous process for the oxidation of cyclohexane to adipic acid, using a gas containing oxygen, in a liquid medium comprising a carboxylic acid as solvent and in the presence of a catalyst containing at least cobalt, characterized in that it includes the following steps:

a) the actual oxidation of the cyclohexane to adipic acid, b) the reaction mixture derived from the oxidation of the cyclohexane to adipic acid is treated in order to remove the more volatile compounds, optionally after crystallization and separation of at least some of the adipic acid which it contains, c) the residue obtained is extracted using a solvent chosen from ketones, alcohols, esters, various mixtures thereof or mixtures of hydrocarbon and carboxylic acid, which solvent is capable of dissolving all or a large part of the diacids contained in the said residue, d) the extraction residue thus obtained, containing the larger part of the cobalt catalyst, is used in a new cyclohexane oxidation operation a).

Each of the various steps of this continuous process has been outlined above and reference may be made to this description for the particular embodiments of the process.

A fourth subject of the invention consists of a continuous process for the oxidation of cyclohexane to adipic acid, using a gas containing oxygen, in a liquid medium comprising acetic acid as solvent and in the presence of a catalyst containing at least cobalt, characterized in that it includes the following steps:

a) the actual oxidation of the cyclohexane to adipic acid,
b) either: b1) cooling of the crude final reaction mixture, optionally after concentrating, in order to crystallize at least some of the adipic acid, separation of the said adipic acid by filtration or centrifugation and then, if necessary, separation by settling of the filtrate or of the centrifugate obtained into a cyclohexane phase and an acetic phase,
   or: b2) removal of the crude final reaction mixture while hot, the maid reaction mixture being a two-phase or a monophase mixture, its possible separation by settling into a cyclohexane phase and an acetic phase, cooling of the acetic phase which has been separated by settling or, where appropriate, of the single acetic phase so as to crystallize at least some of the adipic acid, and separation by filtration or centrifugation of the said adipic acid and of the acetic phase,
   or: b3) removal of the water from the reaction mixture during the oxidation step a), by distillation of the cyclohexane/water azeotrope and optional reintroduction of the distilled cyclohexane into the reactor, followed by treatment of the crude final reaction mixture according to the variant b1), the said treatment giving, in this came, a single liquid phase which is treated in the same way as an acetic phase for the remainder of the process,
c) concentration of the acetic phase in order to remove therefrom at least the majority of the water, if this has not been done in the variant b3),
d) extraction of the acetic phase using cyclohexane or a cyclohexane/acetic acid mixture in an amount such that, in the cyclohexane/acetic phase mixture, the overall cyclohexane/acetic acid weight ratio is between 1/1 and 50/1 and preferably between 2/1 and 15/1,
e) separation of a cyclohexane solution containing at least some of the glutaric acid and succinic acid, on the one hand, and of a mixture essentially containing the cobalt catalyst, on the other hand,
f) recycling of the mixture containing the cobalt catalyst in a new oxidation reaction a).

Each of the various steps of this continuous process has been outlined above and reference may be made to this description for the particular embodiments of the process.

The examples which follow illustrate the present invention.

EXAMPLES 1 TO 5

The compounds given below are charged, at room temperature, into a titanium-sleeved 1.5 liter autoclave which has been pre-purged with nitrogen and which is fitted with a six-blade double turbine and various openings for introduction of the reagents and the fluids or for removal of the reaction products and the fluids:

cobalt acetate tetrahydrate: 4.0 g (16 mmol)

acetic acid: 359 g (5.98 mol)

cyclohexane: 289.7 g (3.45 mol)

acetaldehyde: 1.2 g (27.3 mmol).

After closing the autoclave, the nitrogen pressure is brought to 20 bar, stirring is started at 800 revolutions/min and the temperature is brought to 102° C. over 29 min. The nitrogen is then replaced by 20 bar of depleted air (5.85% oxygen). The outlet gas flow rate is set at 250 liters/hour.

After about 10 min of induction, during which there is no oxygen consutption, the temperature rises suddenly to 106° C. and the oxygen starts to be consumed. When the oxygen content of the air at the autoclave outlet reaches 1%, the supply of depleted air at an oxygen content of 5.85% is replaced by a supply of air at an oxygen content of 11.35%. The oxygen content at the reactor outlet remains below 1% throughout the test. The average temperature in the autoclave is maintained at 106°–107° C.

When 50 liters of oxygen have been consumed, the outlet valve and the air supply are closed. At the same time, the temperature in the autoclave is gradually brought to 75° C.

The reaction mixture is then recovered using a withdrawal valve connected to a dipping tube, and is then rapidly cooled to about 20° C.

A three-phase medium is obtained, consisting of crude adipic acid which has precipitated (49 g) , an acetic phase (451.4 g) and a cyclohexane phase (143.2 g) the autoclave is rinsed with acetic acid and this rinsing liquid is added to the acetic phase. The contents of a trap (5.5 g) placed after a condenser are added to the cyclohexane phase.

On recrystallization from acetic acid, 294.5 mal of recrystallized adipic acid are obtained, as well as 38.5 mmol of adipic acid, 1.6 mmol of glutaric acid and 1.2 mmol of succinic acid which are dissolved. About 5% of the catalyst, which has been entrained by precipitation of the adipic acid, are recovered in the acetic acid from the recrystallization and this acetic solution is added to the acetic phase.

The acetic and cyclohexane phases are assayed by gas chromatography.

The results of Example 1 and of the comparative tests or examples which follow are expressed in the following way:
  degree of conversion (DC) of the cyclohexane: mol % of the cyclohexane converted into the various compounds of the final reaction mixture;
  selectivity (RT) towards product P: moles of product P×100/moles of cyclohexane converted:
  linearity of diacids formed (Lty): moles of adipic acid formed×100/sum of the moles of the adipic, glutaric and succinic acids formed.

The acetic phase contains virtually all of the acids and lactones formed and the very large majority of the cyclohexanol, the cyclohexanone and the cyclohexyl acetate which are formed, as well as the water and virtually all of the catalyst.

The acetic phase is concentrated by heating to 50° C., at reduced pressure (4 kPa) in order to remove the water and some of.the acetic acid, cyclohexane, cyclohexanol and cyclohexanone, until a solution containing 110 g of acetic acid and 35 g of products (essentially the diacids and the cobalt catalyst) is obtained.

This concentrated acetic phase in treated with 1300 g of cyclohexane at 70° C. A red precipitate and a colourless supernatant liquid appear, the liquid being removed while hot (60° C.).

The supernatant contains most of the oxidation products (diacids, cyclohexanol, cyclohexanone, esters and lactones) whereas the precipitate contains more than 95% of the cobalt (amount determined by assay on a sample) which is returned to the reactor with the extra cobalt, cyclohexane and acetic acid necessary to reestablish the proportions indicated above for the first test.

The catalyst is successively recycled 4 times (Examples 2 to 5).

The results obtained with Examples 1 to 5 are collated in Table 1 below.

In this table, the following new abbreviations are used:
  AdOH for adipic acid
  olone for the cyclohexanol/cyclohexanone mixture O2 for the maximum amount of oxygen consumed in liters/hour (this value represents the maximum rate of oxidation)

Peff for AdOH for production efficiency for adipic acid formed expressed in g/l.h.

TABLE 1

| Examples | Reaction time | O2 in l/min | DC % of the cyclo-hexane | RT % towards AdOH | Peff for AdOH | RT % towards olone | Lty % |
|---|---|---|---|---|---|---|---|
| Example 1 | 125 min | 0.45 | 23.2 | 68.5 | 54.7 | 15.2 | 87.7 |
| Example 2 | 130 min | 0.45 | 23.9 | 67.9 | 53.8 | 14.9 | 86.9 |
| Example 3 | 133 min | 0.44 | 23.5 | 68.3 | 52.0 | 14.5 | 87.1 |
| Example 4 | 130 min | 0.44 | 22.9 | 67.9 | 51.5 | 14.8 | 86.8 |
| Example 5 | 130 min | 0.44 | 34.6 | 68.3 | 55.7 | 13.9 | 86.4 |

It is observed that the catalytic activity, the selectivities towards adipic acid and towards olone (mixture of adipogenic compounds) and the linearity are conserved over 5 successive oxidations.

COMPARATIVE TESTS a TO e

The first oxidation test is performed with the same amounts of reagents and catalyst and the same operating conditions as Example 1, but the treatment of the final reaction mixture is different.

As in Example 1, the acetic phase contains almost all of the acids and lactones formed and the very great majority of the cyclohexanol, cyclohexanone and cyclohexyl acetate which are formed, as well as the water and virtually all of the catalyst (about 5% of the catalyst, which were entrained by precipitation of the adipic acid, are recovered in the acetic acid used for the recrystallization of the adipic acid and thin acetic solution is added to the acetic phase.

The acetic phase is concentrated by heating to 50° C., at a reduced pressure (4 kPa) in order to remove the water and some of the acetic acid, cyclohexane, cyclohezanol and cyclohexanone, until a solution containing 110 g of acetic acid and 35 g of products (essentially the diacids and the cobalt catalyst) is obtained.

This concentrated acetic solution is sent to the reactor with the extra cobalt, cyclohexane and acetic acid necessary to reestablish the proportions indicated above for the first test a.

The catalyst is successively recycled 4 times (comparative tests b, c, d and e).

The results obtained with the tests a to e are collated in Table 2 below.

TABLE 2

| Comparative test | Reaction time | O2 in l/min | DC % of the cyclo-hexane | RT % towards AdOH | Peff for AdOH | RT % towards olone | Lty % |
|---|---|---|---|---|---|---|---|
| Test a | 122 min | 0.46 | 21.7 | 65.4 | 50.1 | 15.0 | 86.8 |
| Test b | 125 min | 0.44 | 21.3 | 69.0 | 50.6 | 9.1 | 84.7 |
| Test c | 130 min | 0.36 | 13.8 | 71.0 | 32.5 | 7.0 | 84.3 |
| Test d | 181 min | 0.30 | 16.2 | 71.1 | 27.4 | 7.6 | 87.7 |
| Test e | 223 min | 0.21 | 15.2 | 69.7 | 20.5 | 9.1 | 85.3 |

It is observed that the overall selectivity is towards adipic acid and olone and the linearity are conserved over 5 successive oxidations. On the other hand, if the activity is conserved during the first recycling of the catalyst, a progressive deactivation of the said catalyst is observed.

In addition, the crude adipic acid which precipitates during cooling of the final reaction mixture is increasingly soiled by the other oxidation products whose concentration rises as the recyclings continue, and this precipitated adipic acid entrains increasingly more cobalt.

EXAMPLE 6

A solution, which in homogeneous at 100° C., containing 120 g of acetic acid, 3.7 g of succinic acid (31.6 mmol), 7.3 g of glutaric acid (55.3 mmol), 29.2 g of adipic acid (200 mmol) and 4 g of cobalt acetate tetrahydrate (16 mmol) is gradually cooled to room temperature.

A solid containing 21 g of adipic acid is separated out by filtration and a filtrate consisting of 116 g of acetic acids 3.0 g of succinic acid (25.4 mmol), 7.0 g of giutaric acid (53 mmol), 8.2 g of adipic acid (56 mmol) and 4 g of cobalt acetate tetrahydrate (16 mmol) is recovered.

This filtrate in concentrated to dryness and then treated with twice 50 ml of hot (56° C.) acetone.

The distribution of the compounds between the acetone extract and the remaining solid residue is indicated in Table 3 below.

TABLE 3

| Compounds | Dry filtrate | Acetone extract | Solid residue after extraction |
|---|---|---|---|
| Succinic acid | 25.4 mmol | 18 mmol (70.9%) | 7.1 mmol (28%) |
| Glutaric acid | 53 mmol | 36.4 mmol (68.7%) | 16.1 mmol (30.4%) |
| Adipic acid | 56 mmol | 45.1 mmol (80.5%) | 10.7 mmol (19.1%) |
| Cobalt | 16 mmol | <0.016 mmol (<0.1%) | 15.9 mmol (99.4%) |

EXAMPLE 7

A solution of the same composition as that of Example 6 is treated in the same way in order to separate out, by crystallization and filtration, the majority of the adipic acid.

The filtrate obtained consists of 115 g of acetic acid, 3.7 g of succinic acid (31 mmol), 7.3 g of glutaric acid (55 mmol), 8.8 g of adipic acid (60 mmol) and 4 g of cobalt acetate tetrahydrate (16 mmol).

This filtrate is concentrated to dryness and then treated with 5 times 100 ml of a hot (70° C.) cyclohexanone/acetic acid mixture (82/18 weight/weight).

The distribution of the compounds between the extract of the solvent mixture and the remaining solid residue is indicated in Table 4 below.

TABLE 4

| Compounds | Dry filtrate | Solvent extract | Solid residue after extraction |
|---|---|---|---|
| Succinic acid | 31 mmol | 16.4 mmol (52.9%) | 14.5 mmol (46.7%) |
| Glutaric acid | 55 mmol | 44.8 mmol (81.5%) | 10.1 mmol (18.4%) |
| Adipic acid | 60 mmol | 42.9 mmol (71.5%) | 17.1 mmol (28.5%) |
| Cobalt | 16 mmol | 0.9 mmol (5.6%) | 15 mmol (93.8%) |

EXAMPLE 8

A solution, which is homogeneous at 100° C., containing 120 g of acetic acid, 3.4 g of succinic acid, 6.3 g of glutaric acid, 29.9 g of adipic acid and 4.1 g of cobalt acetate tetrahydrate is gradually cooled to room temperature.

A solid containing 21.2 g of adipic acid is separated out by filtration and a filtrate consisting of 116 g of acetic acid, 3.2 g of succinic acid (27.1 mmol), 6.2 g of glutaric acid (47 mmol), 8.7 g of adipic acid (60 mmol) and 4.1 g of cobalt acetate tetrahydrate (16.4 mmol) is recovered.

This filtrate is partially concentrated, in order to give a hot solution of about 52 g. This hot concentrated solution is treated by running 168.5 g of acetone therein. The temperature of the mixture stabilizes to 60° C. The mixture consists of a solid and a supernatant liquid, which are separated while hot.

The distribution of the compounds between the supernatant liquid and the separated solid residue is indicated in table 5 below.

TABLE 5

| Compounds | Initial filtrate | Supernatant liquid | Separated solid residue |
| --- | --- | --- | --- |
| Succinic acid | 27.1 mmol | 17.2 mmol (63.5%) | 9.5 mmol (35%) |
| Glutaric acid | 47 mmol | 42.5 mmol (90.4%) | 4.5 mmol (9.6%) |
| Adipic acid | 60 mmol | 55.5 mmol (92.5%) | 4.4 mmol (7.3%) |
| Cobalt | 16 mmol | 0.25 mmol (1.5%) | 15 mmol (98.2%) |

We claim:

1. Process for recycling a catalyst containing cobalt, in a reaction for the direct oxidation of cyclohexane to adipic acid, said process including a step for the treatment of the reaction mixture obtained during the oxidation of the cyclohexane to adipic acid, consisting of an extraction of at least some of the glutaric acid and succinic acid which are formed in the reaction.

2. Process according to claim 1 for recycling a catalyst containing cobalt, in a reaction for the direct oxidation of cyclohexane to adipic acid, in a solvent comprising at least one aliphatic carboxylic acid having only primary or secondary hydrogen atoms, by a gas containing oxygen, wherein:

the crude reaction mixture derived from a prior operation for the oxidation of the cyclohexane to adipic acid is treated in order to remove the more volatile compounds, optionally after the crystallization and separation of at least some of the adipic acid which it contains, the residue obtained is extracted using a solvent, chosen from ketones, alcohols, esters, various mixtures thereof or mixtures of hydrocarbon and carboxylic acid, this solvent being capable of dissolving all or a large part of the diacids contained in the said residue, the extraction residue thus obtained, containing the larger part of the cobalt catalyst, is used in a new operation for the oxidation of cyclohexane to adipic acid, after addition of the necessary complements of cyclohexane, of carboxylic acid and, where appropriate, of cobalt catalyst.

3. Process according to claim 2, wherein the crude reaction mixture is treated by distillation, at atmospheric pressure or at reduced pressure, of the more volatile compounds, the carboxylic acid serving as solvent in the oxidation reaction, the water formed and certain intermediate compounds.

4. Process according to claim 2, wherein the solvent which serves for extraction of the catalyst from the residue obtained is chosen from acetone, methyl ethyl ketone, cyclohexanone, 1-propanol, 2-propanol, 1-butanol, 2-butanol, tert-butanol, cyclohexanol, esters derived from the alcohols mentioned above with aliphatic carboxylic acids having only primary or secondary hydrogen atoms.

5. Process according to claim 1 for recycling a catalyst containing cobalt, in a reaction for the direct oxidation of cyclohexane to adipic acid, by a gas containing oxygen, the crude reaction mixture, obtained from a prior operation of oxidation of the cyclohexane to adipic acid, from which mixture at least some of the intermediate oxidation products, is subjected to at least one extraction using at least one cosolvent or using a mixture comprising a cosolvent and a carboxylic acid, in that there are separated, on the one hand, a mixture containing at least some of the cobalt catalyst, some of the carboxylic acid and possibly residual amounts of other compounds and, on the other hand, a solution containing the cosolvent and at least some of the glutaric acid and succinic acid which are formed in the oxidation reaction, as well an some carboxylic acid, and in that the mixture containing at least some of the cobalt catalyst is used in a new operation for the oxidation of cyclohexane to adipic acid, optionally after the addition of extra cobalt catalyst.

6. Process according to claim 5, wherein the cosolvent used is chosen from aliphatic and cycloaliphatic hydrocarbons, ketones and alcohols.

7. Process according to claim 2, wherein the aliphatic carboxylic acid used is acetic acid.

8. Process according to claim 5, wherein the crude reaction mixture is subjected to cooling to a temperature of 16° C. to 30° C. to bring about the crystallization of at least some of the adipic acid formed, thus giving either a three-phase medium comprising a solid phase essentially consisting of adipic acid, an upper cyclohexane liquid phase and a lower acetic liquid phase, or giving a two-phase medium comprising a solid phase essentially consisting of adipic acid and an acetic phase, followed, if need be, after filtration or centrifugation of the solid, by separation of the two liquid phases after settling.

9. Process according to claim 8, wherein the reaction mixture is concentrated prior to the adipic acid crystallization operation.

10. Process according to claim 5, wherein the crude reaction mixture is removed while hot, the said reaction mixture then being a two-phase or monophase mixture, two liquid phases: an upper cyclohexane phase and a lower acetic liquid phase are separated after settling, if necessary, and the said lower acetic phase or the single acetic phase is cooled to a temperature of 16° C. to 30° C. to bring about the crystallization of at least some of the adipic acid formed, which is then separated out by filtration or centrifugation of the acetic phase.

11. Process according to claim 8, wherein the adipic acid is purified by recrystallization from a suitable solvent, which is then optionally added to the acetic phase obtained above.

12. Process according to claim 2, wherein a water/cyclohexane azeotropic mixture is distilled off during the oxidation reaction, and the cyclohexane is then reintroduced into the reactor after separation of this mixture by settling and the crude reaction mixture is treated.

13. Process according to claim 7, wherein the acetic phase, obtained in the treatment of the crude reaction mixture, is subjected to an extraction with cyclohexane, obtained after separation by settling, or after having been concentrated by heating to a temperature of 30° C. to 80° C. at reduced pressure.

14. Process according to claim 13, characterized in that concentration of the acetic phase reduces this phase to a volume representing from 80% to 10% of its initial volume.

15. Process according to claim 13, characterized in that the acetic phase is concentrated to dryness, that is to say that all of the acetic acid which it contains is removed.

16. Process according to claim 13, wherein the compounds separated from the acetic phase during concentration thereof are recycled in the cyclohexane oxidation step, either in total or after separation of at least some of the water which they contain.

17. Process according to claim 16, wherein the acetic phase is extracted either with cyclohexane alone or with cyclohexane/acetic acid mixtures, so that the acetic phase subjected to the extraction/cyclohexane mixture has an overall cyclohexane/acetic acid weight ratio between 1/1 and 50/1.

18. Process according to claim 17, wherein the extraction is performed one or more times or, within the context of a continuous process, by the usual industrial techniques and in that it is carried out at a temperature ranging up to the boiling point of the solvent or solvents used.

19. Process according to claim 17, wherein the extraction operation gives, on the one hand, a solution which contains at least some of the glutaric acid and succinic acid, as well as residual amounts of other by-products, and, on the other hand, a mixture essentially containing the cobalt catalyst, it being possible for this mixture to be separated by settling.

20. Process according to claim 19, wherein the separated cobalt catalyst is recycled in a new cyclohexane oxidation reaction, optionally after a further addition of the cyclohexane to compensate for the losses suffered during the various treatments of the reaction mixture obtained from the cyclohexane oxidation.

21. Continuous process for the oxidation of cyclohexane to adipic acid, using a gas containing oxygen, in a liquid medium comprising a carboxylic acid as solvent and in the presence of a catalyst containing at least cobalt, comprising the following steps:
  a) the actual oxidation of the cyclohexane to adipic acid,
  b) the reaction mixture derived from the oxidation of the cyclohexane to adipic acid is treated in order to remove the more volatile compounds, optionally after crystallization and separation of at least some of the adipic acid which it contains,
  c) the residue obtained is extracted using a solvent chosen from ketones, alcohols, esters, various mixtures thereof or mixtures of hydrocarbon and carboxylic acid, which solvent is capable of dissolving all or a large part of the diacids contained in the said residue,
  d) the extraction residue thus obtained, containing the larger part of the cobalt catalyst, is used in a new cyclohexane oxidation operation a).

22. Continuous process for the oxidation of cyclohexane to adipic acid, using a gas containing oxygen, in a liquid medium comprising acetic acid as solvent and in the presence of a catalyst containing at least cobalt, comprising the following steps according to one of claim 5,
  a) the actual oxidation of the cyclohexane to adipic acid,
  b) either: b1) cooling of the crude final reaction mixture, optionally after concentrating, in order to crystallize at least some of the adipic acid, separation of the said adipic acid by filtration or centrifugation and then, if necessary, separation by settling of the filtrate or of the centrifugate obtained into a cyclohexane phase and an acetic phase,
  or: b2) removal of the crude final reaction mixture while hot, the said reaction mixture being a two-phase or a monaphase mixture, its possible separation by settling into a cyclohexane phase and an acetic phase, cooling of the acetic phase which has been separated by settling or, where appropriate, of the single acetic phase so as to crystallize at least some of the adipic acid, and separation by filtration or centrifugation of the said adipic acid and of the acetic phase,
  or: b3) removal of the water from the reaction mixture during the oxidation step a), by distillation of the cyclohexane/water azeotrope and optional reintroduction of the distilled cyclohexane into the reactor, followed by treatment of the crude final reaction mixture according to the variant b1), the said treatment giving a single acetic phase
  c) concentration of the acetic phase in order to remove therefrom at least the majority of the water, if this has not been done in the variant b3),
  d) extraction of the acetic phase using cyclohexane or a cyclohexane/acetic acid mixture in an amount such that, in the cyclohexane/acetic phase mixture, the overall cyclohexane/acetic acid weight ratio is between 1/1 and 50/1,
  e) separation of a cyclohexane solution containing at least some of the glutaric acid and succinic acid, on the one hand, and of a mixture essentially containing the cobalt catalyst, on the other hand,
  f) recycling of the mixture containing the cobalt catalyst in a now oxidation reaction a).

23. Process according to claim 3, wherein the more volatile compounds are unreacted cyclohexane.

24. Process according to claim 3, wherein the intermediate compounds are cyclohexanol and cyclohexanone.

25. Process according to claim 4, wherein the aliphatic carboxylic acids having only primary or secondary hydrogen atoms are those which are used in the cyclohexane oxidation reaction, mixtures of several of the extraction solvents and mixtures of aliphatic or cycloaliphatic hydrocarbons and carboxylic acids.

26. Process according to claim 5, wherein the intermediate oxidation products comprise cyclohexanol and cyclohexanone, some carboxylic acid solvent and water has been separated and from which mixture at least some of the adipic acid formed has been recovered by crystallization.

27. Process according to claim 6, wherein the cosolvent is cyclohexane.

28. Process according to claim 11, wherein the solvent is acetic acid or water.

29. Process according to claim 17, wherein the overall cyclohexane/acetic acid weight ratio is between 2/1 and 15/1.

30. Process according to claim 18, wherein the temperature is between 10° C. and 80° C.

* * * * *